US006673755B2

(12) United States Patent
Wei et al.

(10) Patent No.: US 6,673,755 B2
(45) Date of Patent: Jan. 6, 2004

(54) PERSONAL CLEANSING COMPOSITIONS CONTAINING CLEANSING AND SKIN ACTIVE PHASES SEPARATED BY ONE OR MORE PACKAGING BARRIERS

(75) Inventors: Karl Shiqing Wei, Mason, OH (US); John Christopher Wesner, Liberty Township, OH (US); Cheyne Pohlman Thomas, Highland Heights, KY (US); Christopher Dean Putman, West Chester, OH (US); Lourdes Dessus Albacarys, West Chester, OH (US); Edward Dewey Smith, III, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 113 days.

(21) Appl. No.: 10/050,494

(22) Filed: Jan. 16, 2002

(65) Prior Publication Data

US 2003/0144160 A1 Jul. 31, 2003

(51) Int. Cl.$^7$ .......................... C11D 7/50; C11D 17/00; A61K 7/50; A61K 7/48
(52) U.S. Cl. .................. 510/130; 510/140; 510/159
(58) Field of Search ................. 510/130, 139, 510/140, 151, 159

(56) References Cited

U.S. PATENT DOCUMENTS

| | | |
|---|---|---|
| 3,533,955 A | 10/1970 | Pader et al. |
| 5,059,414 A | 10/1991 | Dallal et al. |
| 5,455,035 A | 10/1995 | Guerrero et al. |
| 5,612,307 A | 3/1997 | Chambers et al. |
| 5,929,019 A | 7/1999 | Puvvada et al. |
| 5,947,335 A | 9/1999 | Milio et al. |
| 6,008,181 A * | 12/1999 | Cripe et al. ............... 510/426 |
| 6,136,769 A * | 10/2000 | Asano et al. .............. 510/329 |
| 6,176,391 B1 | 1/2001 | Rehkemper et al. |
| 6,268,322 B1 | 7/2001 | St. Lewis et al. |
| 6,306,806 B1 | 10/2001 | St. Lewis et al. |

FOREIGN PATENT DOCUMENTS

| | | |
|---|---|---|
| GB | 1277324 A | 6/1972 |
| WO | WO 94/10973 A1 | 5/1994 |
| WO | WO 98/27193 A1 | 6/1998 |
| WO | WO 99/38489 A1 | 8/1999 |
| WO | WO 99/38491 A1 | 8/1999 |

\* cited by examiner

*Primary Examiner*—Mark Kopec
*Assistant Examiner*—John M Petruncio
(74) *Attorney, Agent, or Firm*—John M. Howell; Tara M. Rosnell; Karen F. Clark

(57) ABSTRACT

Disclosed are personal cleansing compositions, and corresponding methods of application, wherein the compositions comprise (A) a cleansing phase containing a cleansing surfactant and water; and (B) an active phase containing lipophilic carrier and preferably a skin active agent; wherein the cleansing and active phases are physically separated from one another by one or more packaging barriers, located in the same or separate packages. Preferred embodiments are further defined by selected lipophilic carrier rheologies, defined active phase particulates for improved skin feel, and selected chronic skin active agents for use in the active phase. These compositions and corresponding methods provide improved cosmetics, skin feel, and/or skin active efficacy.

34 Claims, No Drawings

PERSONAL CLEANSING COMPOSITIONS CONTAINING CLEANSING AND SKIN ACTIVE PHASES SEPARATED BY ONE OR MORE PACKAGING BARRIERS

FIELD OF THE INVENTION

The present invention relates to personal cleansing compositions comprising cleansing and skin active phases separated by one or more packaging barriers.

BACKGROUND OF THE INVENTION

Personal cleansing compositions that provide skin and hair conditioning benefits are well known. Many of these compositions are aqueous systems comprising an emulsified conditioning oil or other similar material in combination with a lathering surfactant. Although it is convenient to use a single composition or product that provides both conditioning and cleansing benefits, it is often difficult to formulate a physically stable emulsion that contains an effective combination of a cleansing surfactant and a skin or hair conditioning material.

One attempt at providing conditioning and cleansing benefits from a single personal cleansing product has been the use of dual stream packaging. These packages comprise separate cleansing compositions and conditioning compositions, and then allow for the co-dispensing of the two in a single or dual stream. The separate conditioning and cleansing compositions thus remain separate and physically stable during prolonged storage and just prior to application, but then mix during or after dispensing to provide improved conditioning and cleansing benefits from a physically stable system. Although such dual delivery systems often provide improved conditioning benefits, they also tend to feel greasy or sticky during application and thus leave the skin feeling oily and unclean.

It has now been found that dual delivery systems containing separate cleansing and conditioning streams can be formulated to provide improved cosmetics and skin feel during and after application while also providing excellent skin conditioning and cleansing benefits. It has been found that such a dual delivery system can be formulated with solid non-structuring particulates preferably having an average particle diameter of from about 1 $\mu$m to about 100 $\mu$m. These solid particulates are formulated into the active stream at a concentration of from about 1% to about 90% by weight of the composition, to provide the desired cosmetic and skin feel benefits. It has been found that the use of such particulates in the formulation is especially useful in reducing the greasy and tacky skin feel associated with the use of a separate conditioning stream, while also allowing for the stability benefits and enhanced conditioning benefits associated with the use of such a dual stream system. It has also been found that the above-described particulates are also helpful in improving the cosmetics of other dual delivery systems, wherein the conditioning stream is replaced with a skin active stream, especially a non-aqueous skin active stream.

It has also been found that the dual delivery systems can be formulated as personal cleansing compositions with selected skin active agents that provide improved chronic skin benefits to the desired area of the skin. These compositions comprise a cleansing phase containing a cleansing surfactant and water, and an active phase containing selected chronic skin benefit agents, wherein the cleansing and active phases are physically separated from one another by one or more packaging barriers.

It has also been found that the dual delivery systems can be formulated as personal cleansing and conditioning compositions with improved cosmetics and skin conditioning benefits, wherein the compositions comprise a cleansing phase containing a cleansing surfactant and water, and an active phase containing at least about 10% by weight of a lipophilic material having a solubility parameter of from about 5 to about 10, wherein the active phase has a Consistency Value of from about 1 to about 2,000 poise and a Shear Index of from about 0.1 to about 0.8, and wherein the cleansing and active phases are physically separated and dispensed independently from one another from separate packages, preferably separate packages removably located in a single packaging system or kit.

It has also been found that the personal cleansing and conditioning compositions of the present invention can be packaged in dual stream packaging systems comprising a separate compartment for the conditioning or skin active phase and a separate compartment for the cleansing phase, or they can be packaged in separate packages, including separate packages provided in a kit where each separate package is detachable from the kit and separately dispensable onto the desired application surface.

It is therefore an object of the present invention to provide personal cleansing compositions comprising cleansing and skin active phases that are physically separated from one another by one or more packaging barriers, and which provide improved cosmetics, improved skin active benefits, or combinations thereof.

SUMMARY OF THE INVENTION

The present invention is directed to personal cleansing compositions comprising: (A) a cleansing phase containing a cleansing surfactant and water; and (B) an active phase containing (i) a lipophilic carrier; and (ii) solid, non-structuring, particulates preferably having an average particle diameter of from about 1 $\mu$m to about 100 $\mu$m; wherein the cleansing and active phases are physically separated from one another by one or more packaging barriers. These compositions provide improved cosmetics and skin feel during or after application, especially reduced greasy skin feel. The active phase may further comprise a skin active agent.

The present invention is also directed to personal cleansing compositions comprising: (A) a cleansing phase containing a cleansing surfactant and water; and (B) an active phase containing selected chronic skin benefit agents, wherein the cleansing and active phases are physically separated from one another by one or more packaging barriers. These compositions provide improved cosmetics and skin feel during or after application, and are especially useful in providing improved deposition or effectiveness of selected chronic skin benefit agents to the desired area of the skin.

The present invention is also directed to a method of cleansing the skin by combining two separate compositions: (A) a cleansing phase containing a cleansing surfactant and water; and (B) an active phase containing at least about 10% by weight of a lipophilic material having a solubility parameter of from about 5 to about 10, a Consistency Value of from about 1 to about 2,000 poise, and a Shear Index of from about 0.1 to about 0.8, wherein the cleansing and active phases are located in and dispensed independently from separate packages. These compositions provide improved cosmetics and skin feel during or after application, and are especially useful in providing individual consumer control over the optimal relative amounts of each of the cleansing and active phases to be delivered to the desired area of the skin, depending upon the unique skin care needs of the individual consumer.

DETAILED DESCRIPTION

The personal cleansing compositions and methods of the present invention comprise or are directed to physically separated active and cleansing phases. These and other essential limitations of the compositions and methods of the present invention, as well as many of the optional ingredients suitable for use herein, are described in detail hereinafter.

The term "anhydrous" as used herein, unless otherwise specified, refers to those compositions or materials containing less than about 10%, more preferably less than about 5%, even more preferably less than about 3%, even more preferably zero percent, by weight of water.

The term "volatile" as used herein, unless otherwise specified, refers to those materials having an average boiling point at one (1) atmosphere of pressure (atm) of less than about 250° C., more typically less than about 235° C. at one (1) atm.

The term "ambient conditions" as used herein, unless otherwise specified, refers to surrounding conditions at one (1) atmosphere of pressure, 50% relative humidity, and 25° C.

The term "non-structuring particulates" as used herein refers to solids that when formulated into the active phase of the compositions of the present invention do no increase the phase viscosity by more than a factor of 3, preferably no more than by a factor of 2, as measured by a Brookfield DV-II+viscometer at 1 rpm at 25° C. These non-structuring particulates therefore specifically exclude solid particulates that are commonly used as structurants or gellant materials, except that such materials can be used herein as non-structuring particulates provided that they are used at a concentration and under circumstances that do not result in an increase in phase viscosity as described above, or are otherwise used in the composition for any purpose other than to increase viscosity or structure of the active phase.

The term "personal cleansing composition" as used herein, unless otherwise specified, refers to the compositions of the present invention, wherein the compositions are intended to include only those compositions for topical application to the hair or skin, and specifically excludes those compositions that are directed primarily to other applications such as hard surface cleansing, fabric or laundry cleansing, and similar other applications not intended primarily for topical application to the hair or skin.

The Vaughan Solubility Parameter (VSP) as used herein is a parameter used to define the solubility of lipophilic materials. Vaughan Solubility parameters are well known in the various chemical and formulation arts and typically have a range of from 5 to 25.

The term "Consistency" or "k" as used herein is a measure of lipid viscosity and is used in combination with Shear index, to define viscosity for materials whose viscosity is a function of shear. The measurements are made at 35° C. and the units are poise (equal to 100 cps).

The term "Shear index" or "n" as used herein is a measure of lipid viscosity and is used in combination with Consistency, to define viscosity for materials whose viscosity is a function of shear. The measurements are made at 35° C. and the units are dimensionless.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The personal cleansing compositions and methods of the present invention can comprise, consist of, or consist essentially of, the essential elements and limitations of the invention described herein, as well as any additional or optional ingredients, components, or limitations described herein or otherwise useful in personal cleansing compositions intended for topical application to the hair or skin.

Product Form

The personal cleansing compositions of the present invention are liquid or semi-liquid compositions intended for topical application to the hair or skin. These compositions contain a cleansing phase and an active phase, both of which are described in greater detail hereinafter, and both of which are physically separated from one another by one or more packaging barriers. Optionally, the active phase composition can be packaged separately alone and is used as an additive composition for commercially available liquid personal cleansing compositions to provide enhanced cosmetic and skin benefits.

All of the product forms contemplated for purposes of defining the compositions and methods of the present invention are rinse-off formulations, by which is meant the product is applied topically to the hair or skin and then subsequently and immediately (i.e., within minutes) rinsed away with water, or otherwise wiped off using a substrate or other suitable removal means.

The compositions of the present invention are not intended for, and specifically exclude, leave-on formulations and applications.

Packaging Barriers

The compositions of the present invention comprise one or more packaging barriers that provide physical separation between the active phase and the cleansing phase of the compositions. The packaging barrier can be any physical barrier that is attached or fixed to the composition package, or otherwise associated with the package in maintaining separation between the two defined phases. The packaging barriers can be in the same or different packages, and thus the active and cleansing phases can be in the same or different packages.

The packaging barriers for use in the compositions of the present invention can be derived from or otherwise provided by a dual or multi-compartment package, wherein the package comprises two or more compartments within which the active and cleansing phases are separately located, and between which are one or more packaging barriers defining or helping to define the packaging compartments. Such dual or multi-compartment packages further comprise a dispensing valve, apparatus or other means suitable for dispensing the compositions from the package onto the desired site of application. The various phases making up the compositions can be dispensed through the dispensing valve or apparatus together or separately, through the same or different values or apparatuses, in fixed relative amounts or independent of one another in differing relative amounts.

The packaging barriers for use in the compositions of the present invention can be located in separate packages, and thus the active and cleansing phases can be located in separate packages, preferably separate packages removably located or positioned in a single packaging system or kit. In this context, the single packaging system or kit includes a package within which a separate cleansing phase is contained, and a package within which a separate active phase is contained, and wherein the two packages are removably located in a kit for dispensing together at the desired ratios from separate packages.

Non-limiting examples of suitable dual or multi-compartment packages for use with the compositions of the present invention are described in U.S. Pat. No. 5,947,335 (Milio et al.); U.S. Pat. No. 6,176,391 (assigned to Pechiney Plastic Packaging Inc.); U.S. Pat. No. 5,137,178 (Stokes et al.); U.S. Pat. No. 4,773,562 (Gueret); U.S. Pat. No. 4,791,149 (Pocknell); U.S. Pat. No. 4,826,048 (Skorka); U.S. Pat. No. 3,704,812 (Marand); and U.S. Pat. No. 5,385,270 (Cataneo et al.), which descriptions are incorporated herein by reference.

Cleansing Phase

The personal cleansing compositions of the present invention comprise an aqueous cleansing phase that contains a surfactant suitable for application to the hair or skin. Suitable surfactants for use herein include any known or otherwise effective cleansing surfactant suitable for application to the hair or skin, and which is otherwise compatible with the other essential ingredients in the aqueous cleansing phase of the compositions. Suitable cleansing surfactants include anionic, nonionic, cationic, zwitterionic or amphoteric surfactants, or combinations thereof.

The cleansing phase of the personal cleansing compositions of the present invention preferably comprise from about 50% to about 99.9%, more preferably from about 70% to about 95%, of water by weight of the cleansing phase; and a suitable cleansing surfactant at concentrations preferably ranging from about 0.1% to about 50%, more preferably from about 4% to about 30%, even more preferably from about 5% to about 25%, by weight of the cleansing composition.

Anionic surfactants suitable for use in the cleansing phase include alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium or triethanolamine. The alkyl ether sulfates are typically made as condensation products of ethylene oxide and monohydric alcohol's having from about 8 to about 24 carbon atoms. Preferably, R has from about 10 to about 18 carbon atoms in both the alkyl and alkyl ether sulfates. The alcohol's can be derived from fats, e.g., coconut oil or tallow, or can be synthetic. Lauryl alcohol and straight chain alcohol's derived from coconut oil are preferred herein. Such alcohol's are reacted with about 1 to about 10, preferably from about 3 to about 5, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the cleansing phase are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula $[R^1—SO_3—M]$, wherein $R^1$ is chosen from the group consisting of a straight or branched chain, saturated aliphatic hydrocarbon radical having from about 8 to about 24, preferably about 10 to about 18, carbon atoms; and M is a cation. Preferred examples include the salts of an organic sulfuric acid reaction product of a hydrocarbon of the methane series, including iso-, neo-, neso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Additional examples of suitable anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other suitable anionic surfactants of this variety are described in U.S. Pat. Nos. 2,486,921; 2,486,922; and 2,396,278; which descriptions are incorporated herein by reference.

Still other suitable anionic surfactants are the succinamates, examples of which include disodium N-octadecylsulfosuccinamate; diammoniumlauryl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having from about 12 to about 24 carbon atoms. The term "olefin sulfonates" is used herein to mean compounds which can be produced by the sulfonation of a-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The a-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

Another class of anionic surfactants suitable for use in the cleansing phase of the cleansing compositions of the present invention is the b-alkyloxy alkane sulfonates, which conform to the formula:

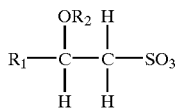

wherein $R_1$ is a straight chain alkyl group having from about 6 to about 20 carbon atoms, $R_2$ is a lower alkyl group having from about 1 to about 3 carbon atoms, preferably 1 carbon atom, and M is a water-soluble cation.

Other suitable surfactants for use in the cleansing phase of the compositions herein are described in *McCutcheon's, Emulsifiers and Detergents*, 1989 Annual, published by M. C. Publishing Co., and in U.S. Pat. No. 3,929,678, which descriptions are incorporated herein by reference.

Preferred anionic surfactants for use in the cleansing phase of the compositions herein include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Amphoteric surfactants suitable for use in the cleansing phase of the compositions herein include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Non-limiting examples of such surfactants include sodium 3-dodecyl-aminopropionate, sodium 3-dodecylaminopropane sulfonate, sodium lauryl sarcosinate, N-alkyltaurines such as those prepared by reacting dodecylamine with sodium isethionate according to the teaching of U.S. Pat. No. 2,658,072, N-higher alkyl aspartic acids such as those prepared in accordance with the teaching of U.S. Pat. No. 2,438,091, and the products described in U.S. Pat. No. 2,528,378, which teachings and descriptions are incorporated herein by reference.

Cationic surfactants can also be used in the cleansing phase of the compositions herein, but are generally less preferred, and preferably represent less than about 5% by weight of the compositions.

Suitable nonionic surfactants for use in the cleansing phase of the compositions herein include condensation products of alkylene oxide groups with an organic hydrophobic compound, which may be aliphatic or alkyl aromatic in nature. Preferred classes of nonionic surfactants include:

1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the ethylene oxide being present in amounts equal to from about 10 to about 60 moles of ethylene oxide per mole of alkyl phenol;

2) nonionic surfactants derived from the condensation of ethylene oxide with the product resulting from the reaction of propylene oxide and ethylene diamine products;

3) condensation products of aliphatic alcohol's having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

4) long chain tertiary amine oxides corresponding to the following general formula:

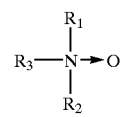

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals;

5) long chain tertiary phosphine oxides corresponding to the following general formula:

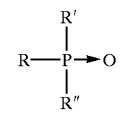

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms;

6) long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety;

7) alkyl polysaccharide (APS) surfactants such as the alkyl polyglycosides, as described in U.S. Pat. No. 4,565,647, which have a hydrophobic group with about 6 to about 30 carbon atoms and polysaccharide (e.g., polyglycoside) as the hydrophilic group, and optionally have a polyalkylene-oxide group joining the hydrophobic and hydrophilic moieties, wherein the alkyl group (i.e., the hydrophobic moiety) can be saturated or unsaturated, branched or unbranched, and unsubstituted or substituted (e.g., with hydroxy or cyclic rings); and 8) polyethylene glycol (PEG) glyceryl fatty esters, such as those of the formula $R(O)OCH_2CH(OH)CH_2(OCH_2CH_2)_nOH$ wherein n is from about 5 to about 200, preferably from about 20 to about 100, and R is an aliphatic hydrocarbyl having from about 8 to about 20 carbon atoms.

Zwitterionic surfactants suitable for use in the cleansing phase of the compositions herein include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. These zwitterionic surfactants include those represented by the formula:

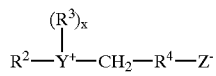

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use in the cleansing phase of the compositions herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Active Phase

The personal cleansing compositions of the present invention comprise an active phase containing a selectively defined lipophilic carrier, and preferably a skin active agent suitable for application to the hair or skin. The active phase is preferably a single or multi-phase liquid within which the skin active agent is suspended, dispersed or otherwise dissolved in the selectively defined lipophilic carrier.

Suitable skin active agents for use herein include any known or otherwise effective skin active agent suitable for application to the hair or skin, and which is otherwise compatible with the other essential ingredients in the active phase of the compositions. Preferred are those skin active agents that provide chronic skin benefits.

The active phase also comprises at least about 10% by weight of one or more lipophilic carriers having a defined Vaugh Solubility Parameter. The lipophilic carriers for use in the active phase are preferably selected among those having defined rheological properties as described hereinafter.

The lipophilic carriers and skin active agents suitable for use in the active phase of the composition are described hereinafter in detail.

1) Lipophilic Carrier

The lipophilic carrier or carriers for use in the active phase of the composition have a Vaughn Solubility Parameter of from about 5 to about 10, and collectively represent from about 10% to about 99% by weight of the active phase. The lipophilic carriers are preferably selected among those having defined rheological properties as described hereinafter, including selected Consistency (k) and Shear Index (n). These preferred Theological properties are especially useful in providing the personal cleansing compositions with improved performance, including improved cosmetic and active efficacy benefits.

A) Vaughan Solubility Parameter Value (VSP)

The lipophilic carrier for use in the active phase of the composition has a Vaughan Solubility Parameter (VSP) of from about 5 to about 10, preferably from about 6 to less than 10, more preferably from about 6 to about 9. These solubility parameters are well known in the formulation arts, and are defined by *Vaughan in Cosmetics and Toiletries,* Vol 103, p47–69, October 1988.

Non-limiting examples of lipophilic carriers having VSP values ranging from about 5 to about 10 include the following:

| VAUGHAN SOLUBILITY PARAMETERS* | |
|---|---|
| Cyclomethicone | 5.92 |
| Squalene | 6.03 |
| Petrolatum | 7.33 |
| Isopropyl Palmitate | 7.78 |
| Isopropyl Myristate | 8.02 |
| Castor Oil | 8.90 |
| Cholesterol | 9.55 |

*As reported in Solubility, Effects in Product, Package, Penetration and Preservation, C. D. Vaughan, Cosmetics and Toiletries, Vol. 103, October 1988.

B) Rheology

The lipophilic carrier or carriers for use in the active phase of the composition have a preferred rheology profile as defined by Consistency (k) and Shear Index (n). Preferred Consistency and Shear Index ranges of are as follows:

| Range | k<br>poise (1/sec)n-1 | n<br>(dimensionless) |
|---|---|---|
| Most preferred | 50–1000 | 0.20–0.4 |
| More Preferred | 10–1000 | 0.1–0.5 |
| Preferred | 1–2000 | 0.1–0.8 |

The lipophilic carriers can be characterized by Consistency (k) and Shear Index (n) values as defined by the above-described ranges, wherein these defined ranges are selected to provide enhanced deposition and reduced stickiness during and after application of the personal cleaning composition on hair or skin.

The Shear index (n) and Consistency (k) values are well known and accepted industry standards for reporting the viscosity profile of materials having a viscosity that is a function of an applied shear rate. The viscosity ($\mu$) for any material can be characterized by the relationship or equation $$[\mu = \sigma/\gamma']$$

wherein $\sigma$ is shear stress and $\gamma'$ is shear rate, so that the viscosity for any material can be measured by either applying a shear rate and measuring the resultant shear stress or vice versa.

The Carrimed CSL 100 Controlled Stress Rheometer is used to determine Shear Index, n, and Consistency, k, for the lipophilic carriers herein. The determination is performed at 35° C. with the 4 cm 2° cone measuring system typically set with a 51 micron gap and is performed via the programmed application of a shear stress (typically from about 0.06 dynes/sq. cm to about 5,000 dynes/sq. cm) over time. If this stress results in a deformation of the sample, i.e. strain of the measuring geometry of at least 10-4 rad/sec, then this rate of strain is reported as a shear rate. These data are used to create a viscosity ($\mu$) versus shear rate ($\gamma'$) flow curve for the lipophilic carrier material. This flow curve can then be modeled in order to provide a mathematical expression that describes the material's behavior within specific limits of shear stress and shear rate. These results were fitted with the following well-accepted power law model (see for instance: *Chemical Engineering,* by Coulson and Richardson, Pergamon, 1982 or *Transport Phenomena* by Bird, Stewart and Lightfoot, Wiley, 1960):

$$[\mu = k\,(\gamma')^{n-1}]$$

The Carrimed CSL 100 Controlled Stress Rheometer is used to perform oscillatory tests at 35° C. with the 4 cm 2° cone measuring system typically set with a 51 micron gap. The oscillatory tests at 35° C. are carried out in 2 steps. The first step is a stress amplitude sweep at the expected starting and ending frequencies for the frequency sweep. These tests allow a determination to be made as to whether or not the test conditions are within the linear viscoelastic region for the test material over the anticipated frequency range. The linear viscoelastic region is a region where there is a linear relationship between stress and strain. The second step is a frequency sweep made at a stress level within that linear viscoelastic region. The frequency sweep allows the test material's viscoelastic behavior to be measured. The oscillatory test on a controlled stress rheometer is performed by applying a stress in an oscillatory manner and measuring the resulting oscillatory strain response and the phase shift between the applied stress wave form and the resulting strain wave form in the test material. The resulting complex modulus is expressed as a combination of the material's elastic (G') and viscous (G") components. The elastic modulus G' is a measure of a materials ability to store recoverable energy. This energy storage can be the result of the ability of a complex polymer, structural network, or a combination of these to recover stored energy after a deformation. The viscous or loss modulus G" is a measure of the unrecoverable energy which has been lost due to viscous flow.

The lipophilic carriers suitable for use herein can include a variety of hydrocarbons oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin and its derivatives, wax esters, beeswax derivatives, sterols and phospholipids, and combinations thereof.

Non-limiting examples of hydrocarbon oils and waxes suitable for use herein include petrolatum, mineral oil, micro-crystalline waxes, polyalkenes, paraffins, cerasin, ozokerite, polyethylene, perhydrosqualene, and combinations thereof.

Non-limiting examples of silicone oils suitable for use as lipophilic carriers herein include dimethicone copolyol, dimethylpolysiloxane, diethylpolysiloxane, mixed C1–C30 alkyl polysiloxanes, phenyl dimethicone, dimethiconol, and combinations thereof. Preferred are non-volatile silicones selected from dimethicone, dimethiconol, mixed C1–C30 alkyl polysiloxane, and combinations thereof. Nonlimiting examples of silicone oils useful herein are described in U.S. Pat. No. 5,011,681 (Ciotti et al.), which description is incorporated herein by reference.

Non-limiting examples of diglycerides and triglycerides suitable for use as lipophilic carriers herein include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof.

Non-limiting examples of acetoglyceride esters suitable for use as lipophilic carriers herein include acetylated monoglycerides.

Non-limiting examples of alkyl esters suitable for use as lipophilic carriers herein include isopropyl esters of fatty acids and long chain esters of long chain fatty acids, e.g. cetyl ricinoleate, non-limiting examples of which incloude isopropyl palmitate, isopropyl myristate, cetyl riconoleate and stearyl riconoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as lipophilic carriers herein include oleyl myristate, oleyl stearate, oleyl oleate, and combinations thereof.

Non-limiting examples of lanolin and lanolin derivatives suitable for use as lipophilic carriers herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Still other suitable lipophilic carriers include milk triglycerides (e.g., hydroxylated milk glyceride) and polyol fatty acid polyesters.

Still other suitable lipophilic carries include wax esters, non-limiting examples of which include beeswax and beeswax derivatives, spermaceti, myristyl myristate, stearyl stearate, and combinations thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof.

The active phase of the composition preferably comprises one or more lipophilic carriers, wherein at least 10% by weight of the lipophilic carriers are selected from petrolatum, mineral oil, sunflower seed oil, micro-crystalline waxes, paraffins, ozokerite, polyethylene, polybutene, polydecene and perhydrosqualene, dimethicones, cyclomethicones, alkyl siloxanes, polymethylsiloxanes and methylphenylpolysiloxanes, lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate castor oil, soy bean oil, maleated soy bean oil, safflower oil, cotton seed oil, corn oil, walnut oil, peanut oil, olive oil, cod liver oil, almond oil, avocado oil, palm oil and sesame oil, and combinations thereof. More preferably, at least about 50% by weight of the liophillic carriers are selected from the groups of petrolatum, mineral oil, paraffins, polyethylene, polybutene, polydecene, dimethicones, alkyl siloxanes, cyclomethicones, lanolin, lanolin oil, lanolin wax. The remainder of the lipid is preferably selected from: isopropyl palmitate, cetyl riconoleate, octyl isononanoate, octyl palmitate, isocetyl stearate, hydroxylated milk glyceride and combinations thereof.

It is believed that other lipid-like materials other than the lipophilic carriers as defined herein, including the preferred lipophilic carriers having the rheological properties as also described herein, are either too easily emulsified and hence will not deposit, or are too "stiff" to adhere or deposit on to skin and provide a moisturization or other skin benefit. The preferred rheological properties as described herein are believed to provide improved deposition of the defined lipophilic materials.

2) Solid Particulates

The personal cleansing compositions of the present invention comprise an active phase that preferably contains a solid, non-structuring, particulate preferably having an average particle diameter of from about 1 $\mu$m to about 100 $\mu$m, more preferably from about 5 $\mu$m to about 40 $\mu$m, at concentrations ranging from about 1% to about 90%, more preferably from about 5% to about 40%, even more preferably from about 10% to about 40%, most preferably from about 10% to about 30%, by weight of the skin active phase.

The solid particulates for use in the active phase are non-structuring particulates. In this context, the term non-structuring refers to those solid particulates that do no provide a substantial network structure to a composition, and therefore when formulated into the active phase of the compositions of the present invention do not increase the phase viscosity by more than a factor of 3, preferably no more than by a factor of 2, as measured by a Brookfield DV-II+ viscometer at 1 rpm at 25° C. These non-structuring particulates therefore specifically exclude solid particulates that are commonly used as structurants or gellant materials, except that such materials can be used herein as non-structuring particulates provided that they are used at a concentration and under circumstances that do not result in an increase in phase viscosity as described above, or are otherwise used in the composition for any purpose other than to increase viscosity or structure of the active phase.

It has been found that the solid non-structuring particulates as defined above provide the dual stream compositions of the present invention with improved skin feel benefits. It has been found that when such particulates are used in the skin active phase of the compositions, and are formulated within the above-defined average particle diameter range, and are most typically spherical or platelet shaped, that the solid particulates provide improved cosmetic benefits to compositions.

The solid non-structuring particulates must also remain insoluble in the composition matrix, and can therefore include any inert or skin active solid particulate suitable for topical application to the hair or skin. Many of the other optional materials as described hereinabove can be selected and formulated within the composition as the solid, insoluble, particulate, provided that the formulated solid has the requisite particulate characteristics as defined herein. In this context, the term "insoluble" only means that all or most of the solid non-structuring particulates remain as solid particulates within the finished composition and are not dissolved, and also maintain the above-described average particle size, concentration, and particle morphology.

Non-limiting examples of solid non-suspending particulates for use herein include inorganic powders such as gums, chalk, Fuller's earth, talc, kaolin, iron oxide, mica, sericite, muscovite, phlogopite, synthetic mica, lepidolite, inorganic pigments, biotite, lithia mica, vermiculite, magnesium carbonate, calcium carbonate, aluminum silicate, starch, smectite clays, alkyl and/or trialkyl aryl ammonium smectites, chemically modified magnesium aluminum silicate, organically modified montmorillonite clay, hydrated aluminum silicate, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), and boron nitride; organic powder such as polyamide resin powder (nylon powder), cyclodextrin, polyethylene powder, methyl polymethacrylate powder, polystyrene powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as titanium dioxide, zinc oxide, and magnesium oxide. Other solid particulates fore use herein are described in U.S. Pat. No. 5,688,831 (El-Nokaly et al.) which description is incorporated herein by reference.

Preferred solid non-suspending particulates for use herein are hydrophobically modified corn starch (e.g., trade name Dry-Flo from National Starch) and particulate crosslinked hydrocarbyl-substituted polysiloxane (e.g., tradename Tospearl from GE Silicone). Mixtures of the above particulates may also be used.

Other suitable solid non-structuring particulates for use herein include various moisture, sweat or sebum absorbing powders, non-limiting examples of which include silicas (or silicon dioxides), silicates, carbonates, various organic copolymers, and combinations thereof. The silicates are most typically those formed by the reaction of a carbonate or silicate with an alkali metal, alkaline earth metal, or transition metal, specific non-limiting examples of which include calcium silicate, amorphous silicas, calcium carbonate, magnesium carbonate, zinc carbonate, and combinations thereof. Non-limiting examples of some suitable silicates and carbonates for use herein are described in Van Nostrand Reinhold's *Encyclopedia of Chemistry*, 4$^{th}$ edition, pages 155, 169, 556, and 849 (1984), which descriptions are incorporated herein by reference. Absorbent powders are also described in U.S. Pat. No. 6,004,584 (Peterson et al.), which description is incorporated herein by reference.

Other absorbent powders suitable for use herein include kaolin, mica, talc, starch, modified starch, microcrystalline cellulose (e.g., Avicel from FMC Corporation), or other silica-containing or non-silica-containing powder suitable for absorbing fluids from the applied surface of the body.

2) Chronic Skin Active Agent

The active phase of the compositions of the present invention preferably comprise a chronic skin active agent suitable for use on the skin, and which is otherwise compatible with the other selected ingredients in the active phase of the composition. The chronic skin actives exclude moisturizing and conditioning agent, i.e., the substance that softens the skin (stratum corneum) and keeps it soft by retarding the decrease of its water content and/or protect the skin. The chronic skin actives are furthered described hereinafter in details.

A) Desquamation Actives

The skin active agent for use herein can include desquamation actives, preferred concentrations of which range from about 0.1% to about 10%, more preferably from about 0.2% to about 5%, even more preferably from about 0.5% to about 4%, by weight of the composition. Desquamation actives enhance the skin appearance benefits of the present invention. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett, which description is incorporated herein by reference.

Another desquamation system that is suitable for use herein contains salicylic acid and zwitterionic surfactants and is described in U.S. Pat. No. 5,652,228 to Bissett, which description is incorporated herein by reference. Zwitterionic surfactants such as described in these applications are also useful as desquamatory agents herein, with cetyl betaine being particularly preferred.

B) Anti-Acne Actives

The skin active agent for use herein can also include anti-acne actives, preferred concentrations of which range from about 0.01% to about 50%, more preferably from about 1% to about 20%, by weight of the composition. Non-limiting examples of anti-acne actives suitable for use herein include resorcinol, sulfur, salicylic acid, benzoyl peroxide, erythromycin, zinc, and other similar materials.

Other non-limiting examples of suitable anti-acne actives for use herein are described in U.S. Pat. No. 5,607,980, issued to McAtee et al, which description is incorporated herein by reference.

C) Anti-Wrinkle Actives/Anti-Atrophy Actives

The skin active agent for use herein can also include anti-wrinkle actives or anti-atrophy actives, including sulfur-containing D and L amino acids and their derivatives and salts, particularly the N-acetyl derivatives, a preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, and skin peel agents (e.g., phenol and the like).

Hydroxy acids as skin active agents herein include salicylic acid and salicylic acid derivatives, preferred concentrations of which range from about 0.01% to about 50%, more preferably from about 0.1% to about 10%, even more preferably from about 0.5% to about 2%, by weight of the composition.

Other non-limiting examples of suitable anti-wrinkle actives for use herein are described in U.S. Pat. No. 6,217,888, issued to Oblong et al, which description is incorporated herein by reference.

D) Anti-Oxidants/Radical Scavengers

The skin active agent for use herein can also include anti-oxidants or radical scavengers, preferred concentrations of which range from about 0.1% to about 10%, more preferably from about 1% to about 5%, by weight of the composition.

Non-limiting examples of anti-oxidants or radical scavengers for use herein include ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

E) Chelators

The skin active agent for use herein can also include chelating agents. As used herein, the term "chelating agent" or "chelator" refers to those skin active agents capable of removing a metal ion from a system by forming a complex so that the metal ion cannot readily participate in or catalyze chemical reactions.

The chelating agents as skin active agents for use herein are preferably formulated at concentrations ranging from about 0.1% to about 10%, more preferably from about 1% to about 5%, by weight of the composition. Non-limiting examples of suitable chelating agents are described in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995, which descriptions are incorporated herein by reference.

Preferred chelating agents for use in the active phase of the compositions of the present invention include furildioxime, furilmonoxime, and derivatives thereof.

F) Flavonoids

The skin active agent for use herein includes flavonoid compounds suitable for use on the hair or skin, preferred concentrations of which range from about 0.01% to about 20%, more preferably from about 0.1% to about 10%, more preferably from about 0.5% to about 5%, by weight of the composition.

Non-limiting examples of flavonoids compounds suitable for use as skin active agents include flavanones such as unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1–C8 alkyl, C1–C4 alkoxyl, O-glycoside, and the like or a mixture of these substituents. Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Among these flavanoid compounds, preferred are unsubstituted flavanone, methoxy flavanones, unsubstituted chalcone, 2',4-dihydroxy chalcone, isoflavone, flavone, and mixtures thereof, more preferably soy isoflavones.

Other non-limiting examples of flavanoid compounds suitable for use as skin active agents herein are described in U.S. Pat. Nos. 5,686,082 and 5,686,367, which descriptions are incorporated herein by reference.

G) Anti-Inflammatory Agents

The skin active agent for use in the active phase of the composition can include anti-inflammatory agents, preferred concentrations of which range from about 0.1% to about 10%, more preferably from about 0.5% to about 5%, by weight of the composition.

Non-limiting examples of steroidal anti-inflammatory agents suitable for use herein include corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

Nonsteroidal anti-inflammatory agents are also suitable for use herein as skin active agents in the active phase of the compositions. Non-limiting examples of non-steroidal anti-inflammatory agents suitable for use herein include oxicams (e.g., piroxicam, isoxicam, tenoxicam, sudoxicam, CP-14, 304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac); fenamates (e.g., mefenamic, meclofenamic, flufenamic, niflumic, tolfenamic acids); propionic acid derivatives (e,g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof.

Other non-limiting examples of suitable anti-inflammatory or similar other skin active agents include candelilla wax, bisabolol (e.g., alpha bisabolol), aloe vera, plant sterols (e.g., phytosterol), Manjistha (extracted from plants in the genus Rubia, particularly *Rubia Cordifolia*), and Guggal (extracted from plants in the genus Commiphora, particularly *Commiphora Mukul*), kola extract, chamomile, red clover extract, sea whip extract, and combinations thereof.

Other non-limiting examples of suitable anti-inflammatory or similar other skin active agents include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$–$C_{24}$ saturated or unsaturated esters of the acids, preferably $C_{10}$–$C_{24}$, more preferably $C_{16}$–$C_{24}$. Specific non-limiting examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, disodium 3-succinyloxy-beta-glycyrrhetinate, and combinations thereof.

H) Anti-Cellulite Agents

The skin active agent for use in the active phase of the compositions of the present invention anti-cellulite agents, non-limiting examples of which include xanthine compounds such as caffeine, theophylline, theobromine, aminophylline, and combinations thereof.

I) Topical Anesthetics

The skin active agent for use in the active phase of the compositions of the present invention include topical anesthetics, non-limiting examples of which include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, pharmaceutically acceptable salts thereof, and combinations thereof.

J) Tanning Actives

The skin active agent for use in the active phase of the compositions of the present invention include tanning actives, preferred concentrations of which range from about 0.1% to about 20% by weight of the composition. Non-limiting examples of such tanning agents include dihydroxyacetone, which is also known as DHA or 1,3-dihydroxy-2-propanone.

K) Skin Lightening Agents

The skin active agent for use in the active phase of the compositions of the present invention can include skin lightening agents, preferred concentrations of which range from about 0.1% to about 10%, more preferably from about 0.2% to about 5%, more preferably from about 0.5% to about 2%, by weight of the composition. Non-limiting examples of skin lightening agents suitable for use herein include kojic acid, arbutin, ascorbic acid and derivatives thereof (e.g., magnesium ascorbyl phosphate or sodium ascorbyl phosphate), and extracts (e.g., mulberry extract, placental extract). Non-limiting examples of skin lightening agents suitable for use herein also include those described in WO 95/34280, WO 95/07432, and WO 95/23780.

L) Skin Soothing and Skin Healing Actives

The skin active agent for use in the active phase of the compositions of the present invention include skin soothing and skin healing actives, preferred concentrations of which range from about 0.1% to about 30%, more preferably from about 0.5% to about 20%, still more preferably from about 0.5% to about 10%, by weight of the composition. Non-limiting examples of skin soothing or skin healing actives suitable for use herein include panthenoic acid derivatives (e.g., panthenol, dexpanthenol, ethyl panthenol), aloe vera, allantoin, bisabolol, and dipotassium glycyrrhizinate.

M) Antimicrobial Actives

The skin active agent for use in the active phase of the compositions of the present invention includes antimicrobial actives, preferred concentrations of which range from about 0.001% to about 10%, more preferably from about 0.01% to about 5%, and still more preferably from about 0.05% to about 2%, by weight of the compositions.

Non-limiting examples of antimicrobial actives for use herein includes β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione, clotrimazole, and combinations thereof.

Optional Ingredients

The personal cleansing compositions of the present invention may further comprise other optional ingredients that may modify the physical, chemical, cosmetic or aesthetic characteristics of the compositions or serve as additional "active" components when deposited on the skin. The compositions may also further comprise optional inert ingredients. Many such optional ingredients are known for use in personal care compositions, and may also be used in the personal cleansing compositions herein, provided that such optional materials are compatible with the essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. These optional materials can be used in any aspect of the compositions of the present invention, including either of the active or cleansing phases as described herein.

Optional ingredients for use in the cleansing phase of the compositions of the present invention can include any active phase material as described herein that is also compatible with the selected ingredients in the cleansing phase. Likewise, optional ingredients for use in the active phase of the compositions of the present invention can include any cleansing phase material described herein that is also compatible with the selected ingredients in the active phase.

Other optional ingredients for use in either phase of the composition, preferably the active phase, include silicone elastomer powders and fluids to provide any of a variety of product benefits, including improved product stability, application cosmetics, emolliency, conditioning, and so forth. The concentration of the silicone elastomers in the composition preferably ranges from about 0.1% to about 20%, more preferably from about 0.5% to about 10%, by weight of the composition. In this context, the weight percentages are based upon the weight of the silicone elastomers material itself, excluding any silicone-containing fluid that typically accompanies such silicone elastomers materials in the formulation process. The silicone elastomers suitable for optional use herein include emulsifying and non-emulsifying silicone elastomers, non-limiting examples of which are described in U.S. Ser. No. 09/613,266 (assigned to The Procter & Gamble Company), which description is incorporated herein by reference.

Method of Use

The personal cleansing compositions of the present invention are preferably applied topically to the desired area of the hair or skin in an amount sufficient to provide effective delivery of the skin active agent to the applied surface, or to otherwise provide effective skin conditioning benefits. The compositions are preferably diluted with water prior to, during, or after topical application, and then subsequently rinsed or wiped off of the applied surface, preferably rinsed off of the applied surface using water or a water-insoluble substrate in combination with water.

The present invention is also directed to methods of using the personal cleansing compositions of the present invention, wherein the personal cleansing compositions are applied as a single product stream comprising the active and cleansing phases mixed immediately prior to or during application, or preferably as dual or multi-product streams wherein the cleansing phase defines at least one of the product streams and the active phase separately defines at least one other of the product streams. The different product streams can be dispensed from the same package, e.g., dual or multi-stream package, but are preferably dispensed from separate packages, more preferably separate packages removably located or positioned in a single package system or kit.

The present invention is therefore also directed to methods of cleansing the hair or skin through the above-described application of the compositions of the present invention. The methods of the present invention are also directed to a method of providing effective delivery of the desired skin active agent, and the resulting benefits from such effective delivery as described herein, to the applied surface through the above-described application of the compositions of the present invention.

Method of Manufacture

The personal cleansing compositions of the present invention may be prepared by any known or otherwise effective technique, suitable for making and formulating the desired product form. Specific non-limiting examples of such methods as they are applied to specific embodiments of the present invention are described in the following examples.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

As noted below, the cleansing and active phases of the compositions are formulated separately and packaged as such upon completion. The packaged compositions include dual delivery systems from a single package, wherein the cleansing and active phases are physically separated within the package by one or more packaging barriers. The packaged compositions are also prepared such that the cleansing and active phases are located in separate packages, including separate packages that are removably located in a single package system or kit.

Each of the exemplified compositions provide improved cosmetics during and after application, including reduced greasy or sticky skin feel, and provide improved deposition or effectiveness of the skin active agent deliver from each prepared composition.

Examples 1–4

The following examples described in Table 1 are non-limiting examples of cleansing phase and active phase compositions with solid particulates of the present invention.

TABLE I

Cleansing Phase and Active Phase Compositions

| Ingredient | Example 1 wt % | Example 2 wt % | Example 3 wt % | Example 4 Wt % |
|---|---|---|---|---|
| I. Cleansing Phase Composition | | | | |
| Ammonium Laureth-3 Sulfate | 13.3 | 3.0 | 3.0 | 3.0 |
| Sodium Lauroamphoacetate (Miranol L-32 Ultra from Rhodia) | 6.7 | 16.7 | 16.7 | 16.7 |
| Ammonium Lauryl Sulfate | — | 1.0 | 1.0 | 1.0 |
| Lauric Acid | — | 0.9 | 0.9 | 0.9 |
| Trihydroxystearin (Thixcin R) | — | 2.0 | 2.0 | 2.0 |
| Guar Hydroxypropyltrimonium Chloride (N-Hance 3196 from Aqualon) | 0.7 | 0.17 | 0.75 | 0.75 |
| Guar Hydroxypropyltrimonium Chloride (Jaguar C-17 from Rhodia) | — | 0.58 | — | — |
| Polyquaterium 10 (UCARE polymer JR-30M from Amerchol) | — | 0.45 | — | — |
| Polymethacrylamidopropyl-trimonium Chloride (Polycare 133 from Rhodia) | — | — | 0.24 | — |
| Polyquaternium-39 (Merqurt Plus 3300 from Calgon) | — | — | 0.81 | — |
| PEG 90M (Polyox WSR 301 from Union Carbide) | 0.4 | 0.25 | — | — |
| PEG-14M (Polyox WSR N-3000 H from Union Carbide) | — | 0.45 | 2.45 | 2.45 |
| Linoleamidoprypyl PG-Dimonium Chloride Phosphate Dimethicone (Monasil PLN from Uniqema) | — | — | 1.0 | 4.0 |
| Tripropylene Glycol | 0.8 | — | — | — |
| Glycerin | — | 1.4 | 4.9 | 4.9 |
| Sodium Chloride | 0.3 | 0.3 | 0.3 | 0.3 |

TABLE I-continued

Cleansing Phase and Active Phase Compositions

| Ingredient | Example 1 wt % | Example 2 wt % | Example 3 wt % | Example 4 Wt % |
|---|---|---|---|---|
| Sodium Benzoate | 0.25 | 0.25 | 0.25 | 0.25 |
| Disodium EDTA | 0.13 | 0.13 | 0.13 | 0.13 |
| Glydant | 0.37 | 0.37 | 0.37 | 0.37 |
| Citric Acid | 0.95 | 1.6 | 0.95 | 0.95 |
| Titanium Dioxide | 0.5 | 0.5 | 0.5 | 0.5 |
| Perfume | 1.0 | 0.5 | 0.5 | 0.5 |
| Water | Q.S. | Q.S. | Q.S. | Q.S. |
| II. Active Phase Composition | | | | |
| Petrolatum | 39.9 | 39.9 | 44.9 | 39.9 |
| Mineral Oil | 39.9 | 39.9 | 44.9 | — |
| Sunflower Seed Oil | — | — | — | 39.9 |
| Tospearl 2000 (from GE) | — | 20 | — | — |
| Dry-Flo AF (from National Starch) | 20 | — | 10 | 20 |
| Perfume | 0.2 | 0.2 | 0.2 | 0.2 |

The compositions described above are prepared by conventional formulation and mixing techniques. The cleansing phase composition 1 is prepared by first adding citric acid into water at 1:3 ratio to form a citric acid premix. The following ingredients are then added into the main mixing vessel in the following sequence: ammonium laureth-3 sulfate, citric acid premix, Miranol L-32 Ultra, sodium chloride, sodium benzoate, Disodium EDTA, glydant. Start agitation of the main mixing vessel. In a separate mixing vessel, disperse N-Hance 3196 in water at 1:10 ratio and form a polymer premix. Add the completely dispersed polymer premix into the main mixing vessel with continuous agitation. Disperse Polyox WSR 301 in tripropylene glycol and then add to the main mixing vessel. Then, add the rest of the water, titanium dioxide, and perfume into the batch. Keep agitation until a homogenous solution forms.

The cleansing composition 2 is prepared by first creating the following premixes: citric acid in water premix at 1:3 ratio, Guar polymer premix with Jaguar C-17 and N-Hance 3196 in water at 1:10 ratio, UCARE premix with JR-30M in water at about 1:30 ratio, and Polyox premix with PEG-90M and PEG-14M in Glycerin at about 1:2 ratio. Then, the following ingredients are added into the main mixing vessel: ammonium lauryl sulfate, ammonium laureth-3 sulfate, citric acid premix, Miranol L-32 ultra, sodium chloride, sodium benzoate, Dissolvine NA ×2, lauric acid, Thixcin R, Guar premix, UCARE premix, Polyox Premix, and the rest of water. Heat the vessel with agitation until it reaches 190F. Let it mix for about 10 mix. Cool the batch with a cold water bath with slow agitation until it reaches 110F. Add the following ingredients: Glydant, perfume, Titanium Dioxide. Keep mixing until a homogeneous solution forms.

The cleansing composition 3 is prepared by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, the following ingredients are added into the main mixing vessel: ammonium lauryl sulfate, ammonium laureth-3 sulfate, citric acid premix, Miranol L-32 ultra, sodium chloride, sodium benzoate, Dissolvine NA ×2, lauric acid, Thixcin R, Guar premix, Polyox Premix, Polycare 133, Merquat Plus 3300, Monosil PLN, and the rest of water. Heat the vessel with agitation until it reaches 190F. Let it mix for about 10 mix. Cool the batch with a cold water bath with slow agitation until it reaches 110F. Add the following ingredients: Glydant, perfume, Titanium Dioxide.

Keep mixing until a homogeneous solution forms.

The cleansing composition 4 is prepared by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, the following ingredients are added into the main mixing vessel: ammonium lauryl sulfate, ammonium laureth-3 sulfate, citric acid premix, Miranol L-32 ultra, sodium chloride, sodium benzoate, Dissolvine NA×2, lauric acid, Thixcin R, Guar premix, Polyox Premix, Monasil PLN, and the rest of water. Heat the vessel with agitation until it reaches 190F. Let it mix for about 10 mix. Cool the batch with a cold water bath with slow agitation until it reaches 110F. Add the following ingredients: Glydant, perfume, Titanium Dioxide. Keep mixing until a homogeneous solution forms.

The active phase is prepared by adding petrolatum into a mixing vessel. Heat the vessel to 140F.

Then, add mineral oil or sunflower seed oil and Dry-Flo AF or Tospearl with agitation. Let the vessel cool down with slow agitation and add perfume when the temperature drops below 100F.

The cleansing composition and active composition are packaged in two separate pump bottles. These compositions are separately dispensed from the pump bottles onto an implement (e.g., a puff) and are used to cleanse the skin and at the same time to deliver conditioning benefits to the skin. The present compositions have good lathering characteristics during use and non-greasy after-use skin feel.

Examples 5–8

The following examples described in Table 2 are non-limiting examples of cleansing phase and active phase compositions of the present invention.

TABLE I

Cleansing Phase and Active Phase Compositions

| Ingredient | Example 5 wt % | Example 6 wt % | Example 7 wt % | Example 8 Wt % |
|---|---|---|---|---|
| I. Cleansing Phase Composition | | | | |
| Ammonium Laureth-3 Sulfate | 13.3 | 13.3 | 13.3 | 13.3 |
| Sodium Lauroamphoacetate (Miranol L-32 Ultra from Rhodia) | 6.7 | 6.7 | 6.7 | 6.7 |
| Guar Hydroxypropyltrimonium Chloride (N-Hance 3196 from Aqualon) | 0.7 | 0.7 | 0.7 | 0.7 |
| PEG 90M (Polyox WSR 301 from Union Carbide) | 0.4 | 0.4 | 0.4 | 0.4 |
| Tripropylene Glycol | 0.8 | 0.8 | 0.8 | 0.8 |
| Sodium Chloride | 0.3 | 0.3 | 0.3 | 0.3 |
| Sodium Benzoate | 0.25 | 0.25 | 0.25 | 0.25 |
| Disodium EDTA | 0.13 | 0.13 | 0.13 | 0.13 |
| Glydant | 0.37 | 0.37 | 0.37 | 0.37 |
| Citric Acid | 0.95 | 0.95 | 0.95 | 0.95 |
| Titanium Dioxide | 0.5 | 0.5 | 0.5 | 0.5 |
| Perfume | 1.0 | 1.0 | 1.0 | 1.0 |
| Water | Q.S. | Q.S. | Q.S. | Q.S. |
| II. Active Phase Composition | | | | |
| Petrolatum | 34.9 | 34.9 | 34.9 | 34.9 |
| Mineral Oil | 34.9 | 34.9 | 34.9 | 34.9 |
| Tocopherol Nicotinate | 10 | — | — | 5 |
| Niacinamide | — | 10 | — | — |
| Farnesol | — | — | 10 | 5 |
| Dry-Flo AF | 20 | 20 | 20 | 20 |

TABLE I-continued

Cleansing Phase and Active Phase Compositions

| Ingredient | Example 5 wt % | Example 6 wt % | Example 7 wt % | Example 8 Wt % |
|---|---|---|---|---|
| Perfume | 0.2 | 0.2 | 0.2 | 0.2 |

The compositions described above are prepared by conventional formulation and mixing techniques. The cleansing phase composition is prepared by first adding citric acid into water at 1:3 ratio to form a citric acid premix. The following ingredients are then added into the main mixing vessel in the following sequence: ammonium laureth-3 sulfate, citric acid premix, Miranol L-32 Ultra, sodium chloride, sodium benzoate, Disodium EDTA, glydant. Start agitation of the main mixing vessel. In a separate mixing vessel, disperse N-Hance 3196 in water at 1:10 ratio and form a polymer premix. Add the completely dispersed polymer premix into the main mixing vessel with continuous agitation. Disperse Polyox WSR 301 in tripropylene glycol and then add to the main mixing vessel. Then, add the rest of the water, titanium dioxide, and perfume into the batch. Keep agitation until a homogenous solution forms.

The active phase is prepared by adding petrolatum into a mixing vessel. Heat the vessel to 140F. Then, add mineral oil and Dry-Flo AF, and skin actives (Tocopherol Nicotinate, Niacinamide, Farnesol) with agitation. Let the vessel cool down with slow agitation and add perfume when the temperature drops below 100F.

The cleansing composition and active composition are packaged in two separate pump bottles. These compositions are separately dispensed from the pump bottles onto an implement (e.g., a puff) and are used to cleanse the skin and at the same time to deposit anti-aging active onto the skin. The present compositions have good lathering characteristics during use and non-greasy after-use skin feel.

What is claimed is:

1. Personal cleansing compositions comprising:
   (A) a cleansing phase containing a cleansing surfactant and water;
   (B) an active phase containing
      (i) a lipophilic carrier;
      (ii) solid, non-structuring, particulates;
   wherein the cleansing and active phases are physically separated from one another by one or more packaging barriers.

2. A personal cleansing composition according to claim 1, wherein the lipophilic carrier has a Vaughn Solubility Parameter of from about 5 to about 10.

3. A personal cleansing composition according to claim 1, wherein the lipophilic carrier has a Vaughn Solubility Parameter of from about 6 to about 9.

4. A personal cleansing composition according to claim 1, wherein the lipophilic carrier represents at least about 10% by weight of the active phase.

5. A personal cleansing composition according to claim 1, wherein the lipophilic carrier has a Consistency value of from about 1 poise to about 2,000 poise.

6. A personal cleansing composition according to claim 1, wherein the lipophilic carrier has a Consistency value of from about 50 poise to about 1000 poise.

7. A personal cleansing composition according to claim 1, wherein the lipophilic carrier has a Shear Index of from about 0.1 to about 0.8.

8. A personal cleansing composition according to claim 1, wherein the lipophilic carrier has a Shear Index of from about 0.2 to about 0.4.

9. A personal cleansing composition according to claim 1, wherein the lipophilic carrier represents at least about 50% by weight of the active phase.

10. A personal cleansing composition according to claim 1, wherein at least 10% by weight of the lipophilic carrier is selected from the group consisting of petrolatum, mineral oil micro-crystalline waxes, paraffins, ozokerite, polyethylene, polybutene, polydecene and perhydrosqualene, dimethicones, cyclomethicones, alkyl siloxanes, polymethylsiloxanes and methylphenylpolysiloxanes, lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate castor oil, soy bean oil, sunflower seed oil, maleated soy bean oil, safflower oil, cotton seed oil, corn oil, walnut oil, peanut oil, olive oil, cod liver oil, almond oil, avocado oil, palm oil and sesame oil, and combinations thereof.

11. A personal cleansing composition according to claim 1, wherein at least 10% by weight of the lipophilic carrier is selected from the group consisting petrolatum, mineral oil, paraffins, sunflower seed oil, polyethylene, polybutene, polydecene, dimethicones, alkyl siloxanes, cyclomethicones, lanolin, lanolin oil, lanolin wax, and combinations thereof.

12. A personal cleansing composition according to claim 1, wherein the solid non-structuring particulates have an average particle diameter of from about 1 μm to about 100 μm.

13. A personal cleansing composition according to claim 1, wherein the solid non-structuring particulates represent from about 1% to about 90% by weight of the active phase.

14. A personal cleansing composition according to claim 1, wherein the solid non-structuring particulates represent from about 10% to about 30% by weight of the active phase.

15. A personal cleansing composition according to claim 1, wherein the active phase and the cleansing phase are in separate packages.

16. A personal cleansing composition according to claim 1, wherein the active phase and the cleansing phase are in a dual or multi-stream package.

17. A personal cleansing composition according to claim 1, wherein the active phase and the cleansing phase are in separate packages, and wherein the separate packages are removably positioned in the same packaging kit.

18. A personal cleansing composition according to claim 1, wherein the active phase further comprises a chronic skin benefit agent.

19. A personal cleansing composition according to claim 18, wherein the chronic skin benefit agent is selected from the group consisting of desquamation actives, anti-acne actives, anti-wrinkle and anti-atrophy actives, anti-oxidants and radical scavengers, chelators, flavonoids, anti-inflammatory agents, anti-cellulite agents, topical anesthetics, tanning actives, skin lightening agents, skin soothing and skin healing actives, antimicrobial actives, and combinations thereof.

20. A personal cleansing composition according to claim 19, wherein the lipophilic carrier has a Vaughn Solubility Parameter of from about 5 to about 10.

21. A personal cleansing composition according to claim 19, wherein the lipophilic carrier has a Vaughn Solubility Parameter of from about 6 to about 9.

22. A personal cleansing composition according to claim 19, wherein the lipophilic carrier represents at least about 10% by weight of the active phase.

23. A personal cleansing composition according to claim 19, wherein the lipophilic carrier has a Consistency value of from about 1 poise to about 2,000 poise.

24. A personal cleansing composition according to claim 19, wherein the lipophilic carrier has a Consistency value of from about 50 poise to about 1000 poise.

25. A personal cleansing composition according to claim 19, wherein the lipophilic carrier has a Shear Index of from about 0.1 to about 0.8.

26. A personal cleansing composition according to claim 19, wherein the lipophilic carrier has a Shear Index of from about 0.2 to about 0.4.

27. A personal cleansing composition according to claim 19, wherein the lipophilic carrier represents at least about 50% by weight of the active phase.

28. A personal cleansing composition according to claim 19, wherein at least 10% by weight of the lipophilic carrier is selected from the group consisting of petrolatum, mineral oil micro-crystalline waxes, paraffins, ozokerite, polyethylene, polybutene, polydecene and perhydrosqualene, dimethicones, cyclomethicones, alkyl siloxanes, polymethylsiloxanes and methylphenylpolysiloxanes, lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate castor oil, soy bean oil, sunflower seed oil, maleated soy bean oil, safflower oil, cotton seed oil, corn oil, walnut oil, peanut oil, olive oil, cod liver oil, almond oil, avocado oil, palm oil and sesame oil, and combinations thereof.

29. A personal cleansing composition according to claim 19, wherein at least 10% by weight of the lipophilic carrier is selected from the group consisting petrolatum, mineral oil, sunflower seed oil, paraffins, polyethylene, polybutene, polydecene, dimethicones, alkyl siloxanes, cyclomethicones, lanolin, lanolin oil, lanolin wax, and combinations thereof.

30. A personal cleansing composition according to claim 19, wherein the active phase further comprises solid, non-structuring, particulates represent from about 1% to about 90% by weight of the active phase.

31. A personal cleansing composition according to claim 29, wherein the solid non-structuring particulates represent from about 10% to about 30% by weight of the active phase.

32. A personal cleansing composition according to claim 19, wherein the active phase and the cleansing phase are in separate packages.

33. A personal cleansing composition according to claim 19, wherein the active phase and the cleansing phase are in a dual or multi-stream package.

34. A personal cleansing composition according to claim 19, wherein the active phase and the cleansing phase are in separate packages, and wherein the separate packages are removably positioned in the same packaging kit.

* * * * *

UNITED STATES PATENT AND TRADEMARK OFFICE
CERTIFICATE OF CORRECTION

PATENT NO. : 6,673,755 B2
DATED : January 6, 2004
INVENTOR(S) : Wei et al.

It is certified that error appears in the above-identified patent and that said Letters Patent is hereby corrected as shown below:

Column 6,
Line 13, "neso" should read -- ineso --.

Column 10,
Line 11, "Theological" should read -- rheological --.

Signed and Sealed this

Twenty-second Day of June, 2004

JON W. DUDAS
*Acting Director of the United States Patent and Trademark Office*